United States Patent
Rioux et al.

(10) Patent No.: US 7,282,051 B2
(45) Date of Patent: Oct. 16, 2007

(54) ABLATION PROBE FOR DELIVERING FLUID THROUGH POROUS STRUCTURE

(75) Inventors: Robert F. Rioux, Ashland, MA (US); Robert Garabedian, Tyngsboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 237 days.

(21) Appl. No.: 10/772,040

(22) Filed: Feb. 4, 2004

(65) Prior Publication Data

US 2005/0171526 A1   Aug. 4, 2005

(51) Int. Cl.
*A61B 18/18* (2006.01)

(52) U.S. Cl. .......................... 606/41; 607/105
(58) Field of Classification Search .............. 606/41; 607/101–105
See application file for complete search history.

(56) References Cited

U.S. PATENT DOCUMENTS

| | | | |
|---|---|---|---|
| 4,031,891 A | 6/1977 | Jess | |
| 4,512,768 A | 4/1985 | Rangaswamy | |
| 4,571,244 A | 2/1986 | Knighton | |
| 5,097,843 A | 3/1992 | Soukup et al. | |
| 5,242,441 A * | 9/1993 | Avitall | 606/41 |
| 5,279,569 A | 1/1994 | Neer et al. | |
| 5,456,689 A * | 10/1995 | Kresch et al. | 606/180 |
| 5,462,521 A | 10/1995 | Brucker et al. | |
| 5,507,743 A | 4/1996 | Edwards et al. | |
| 5,643,197 A | 7/1997 | Brucker et al. | |
| 5,697,281 A | 12/1997 | Eggers et al. | |
| 5,697,882 A | 12/1997 | Eggers et al. | |
| 5,728,143 A | 3/1998 | Gough et al. | |
| 5,868,740 A | 2/1999 | LeVeen et al. | |
| 5,876,340 A * | 3/1999 | Tu et al. | 600/439 |
| 5,913,856 A * | 6/1999 | Chia et al. | 606/41 |

(Continued)

FOREIGN PATENT DOCUMENTS

WO   WO95/17222   6/1995

OTHER PUBLICATIONS

Ahmed, Muneeb, MD, et al "Improved Coagulation with Saline Solution Pretreatment during Radiofrequency Tumor Ablation in a Canine Model" J Vasc Interv Radiol 2002; 13: 717-724.

(Continued)

*Primary Examiner*—Michael Peffley
(74) *Attorney, Agent, or Firm*—Vista IP Law Group LLP

(57) ABSTRACT

Ablation probes are provided for perfusing the tissue, while the tissue is ablated. The ablation probe comprises an elongated shaft and an ablative element, such as a needle electrode. The ablation probe further comprises a lumen that extends through the probe shaft, which will be used to deliver a fluid to the distal end of the probe shaft for perfusion into the surrounding tissue. The ablation probe further comprises a porous structure that is associated with the distal end of the shaft in fluid communication with the lumen. For example, the distal end of the shaft, or the entirety of the shaft, can be composed of the porous structure. Or, if the ablative element is an electrode, the electrode can be composed of the porous structure. Because the pores within the porous structure are pervasive, the fluid will freely flow out into the tissue notwithstanding that some of the pores may become clogged.

56 Claims, 5 Drawing Sheets

U.S. PATENT DOCUMENTS

| | | | |
|---|---|---|---|
| 5,961,513 A | 10/1999 | Swanson et al. | |
| 6,017,338 A * | 1/2000 | Brucker et al. | 606/41 |
| 6,071,280 A | 6/2000 | Edwards et al. | |
| 6,099,526 A | 8/2000 | Whayne et al. | |
| 6,210,411 B1 | 4/2001 | Hofmann et al. | |
| 6,217,554 B1 | 4/2001 | Green | |
| 6,217,576 B1 * | 4/2001 | Tu et al. | 606/41 |
| 6,231,570 B1 | 5/2001 | Tu et al. | |
| 6,235,022 B1 | 5/2001 | Hallock et al. | |
| 6,235,023 B1 | 5/2001 | Lee et al. | |
| 6,241,710 B1 | 6/2001 | Van Tassel et al. | |
| 6,277,115 B1 | 8/2001 | Saasat | |
| 6,379,353 B1 | 4/2002 | Nichols | |
| 6,425,887 B1 | 7/2002 | McGuckin et al. | |
| 6,475,213 B1 | 11/2002 | Whayne et al. | |
| 6,503,225 B1 | 1/2003 | Kirsch et al. | |
| 6,602,242 B1 * | 8/2003 | Fung et al. | 604/528 |
| 6,666,864 B2 * | 12/2003 | Bencini et al. | 606/41 |
| 6,669,692 B1 * | 12/2003 | Nelson et al. | 606/41 |
| 2001/0001819 A1 | 5/2001 | Lee et al. | |
| 2002/0183638 A1 | 12/2002 | Swanson | |
| 2003/0078573 A1 | 4/2003 | Truckai et al. | |
| 2004/0215185 A1 | 10/2004 | Truckai et al. | |
| 2005/0055019 A1 | 3/2005 | Skarda | |
| 2005/0059964 A1 | 3/2005 | Fitz | |

OTHER PUBLICATIONS

Boehm, Thomas, MD, et al "Radio-frequency Tumor Ablation: Internally Cooled Electrode versus Saline-enhanced Technique in an Aggressive Rabbit Tumor Model" Radiology 2002; 222: 805-813.

PCT International Search Report for PCT/US2005/000483, applicant: Scimed Life Systems, Inc., Forms PCT/ISA/210 and 220, dated Apr. 14, 2005 (7 pages).

PCT Written Opinion of the International Search Authority for PCT/US2005/000483, Applicant: Scimed Life Systems, Inc., Form PCT/ISA/237, dated Apr. 14, 2005 (4 pages).

PCT International Search Report for PCT/US2004/032465, Applicant: Scimed Life Systems, Inc., Forms PCT/ISA/210 and 220, dated Mar. 14, 2005 (9 pages).

PCT Written Opinion of the International Search Authority for PCT/US2004/032465, Applicant: Scimed Life Systems, Inc., Form PCT/ISA/237, dated Mar. 14, 2005 (4 pages).

* cited by examiner

ABLATION PROBE FOR DELIVERING FLUID THROUGH POROUS STRUCTURE

FIELD OF THE INVENTION

The field of the invention relates generally to the structure and use of radio frequency (RF) electrosurgical probes for the treatment of tissue.

BACKGROUND OF THE INVENTION

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. In theory, RF ablation can be used to sculpt precisely the volume of necrosis to match the extent of the tumor. By varying the power output and the type of electrical waveform, it is possible to control the extent of heating, and thus, the resulting ablation. The second technology utilizes multiple needle electrodes, which have been designed for the treatment and necrosis of tumors in the liver and other solid tissues. In general, a multiple electrode array creates a larger lesion than that created by a single needle electrode.

The size of tissue coagulation created from a single electrode, and to a lesser extent a multiple electrode array, has been limited by heat dispersion. As a result, multiple probe insertions must typically be performed in order to ablate the entire tumor. This process considerably increases treatment duration and patient discomfort and, due in large part to the limited echogenicity of the ablation probe when viewed under ultrasonography, requires significant skill for meticulous precision of probe placement. In response to this, the marketplace has attempted to create larger lesions with a single probe insertion. Increasing generator output, however, has been generally unsuccessful for increasing lesion diameter, because an increased wattage is associated with a local increase of temperature to more than 100° C., which induces tissue vaporization and charring. This then increases local tissue impedance, limiting RF deposition, and therefore heat diffusion and associated coagulation necrosis.

It has been shown that the introduction of saline into targeted tissue increases the tissue conductivity, thereby creating a larger lesion size. Currently, this is accomplished by treating the tissue with a separate syringe. See, e.g., Ahmed, et al., Improved Coagulation with Saline Solution Pretreatment during Radiofrequency Tumor Ablation in a Canine Model, J Vasc Interv Radio 2002, July 2002, pp. 717-724; Boehm, et al., Radio-frequency Tumor Ablation: Internally Cooled Electrode Versus Saline-enhanced Technique in an Aggressive Rabbit Tumor Model, Radiology, March 2002, pp. 805-813; and Goldberg et al., Saline-Enhanced Radio-Frequency Tissue Ablation in the Treatment of Liver Metastases, Radiology, January 1997, pp. 205-210. Treating the tissue with a separate syringe, however, is not the most efficient and least invasive manner to deliver saline to the target tissue, since it requires an additional needle insertion and does not anticipate the tissue locations where the ablations will ultimately be performed.

It has also been shown that, during an ablation procedure, a needle electrode can be used to perfuse saline (whether actively cooled or not) in order to reduce the local temperature of the tissue, thereby minimizing tissue vaporization and charring. A needle, however, typically cannot deliver the amount of saline necessary to significantly increase the conductivity of the tissue, either due to an insufficient number or size of perfusion openings within the needle electrode and/or the occurrence of clogged openings resulting from the entrapment of tissue during introduction of the probe.

Thus, there is a need for an improved ablation probe that can maximize the delivery of fluid to tissue in order to provide a more efficient, effective, and dynamic ablation treatment of tissue.

SUMMARY OF THE INVENTION

In accordance with the present inventions, an ablation probe is provided. The ablation probe comprises an elongated shaft, which in the preferred embodiment, is rigid, so that it can be percutaneously or laparoscopically introduced into a patient's body. Alternatively, the probe shaft can be flexible, e.g., if the ablation probe takes the form of an intravascular or extravascular catheter. The ablation probe further comprises an ablative element Although many types of ablative elements may be contemplated by the present invention, the ablative element preferably takes the form of electrode(s), e.g., a single needle electrode or an array of electrodes. The ablation probe further comprises a lumen that extends through the probe shaft, which will be used to deliver a fluid to the distal end of the probe shaft for perfusion into the surrounding tissue.

The ablation probe further comprises a porous structure that is associated with the distal end of the shaft in fluid communication with the lumen. For example, the distal end of the shaft, or the entirety of the shaft, can be composed of the porous structure. Or, if the ablative element is an electrode, the electrode can be composed of the porous structure. In this case, the porous structure is preferably composed of an electrically conductive material, such as stainless steel, so that it is capable of conveying radio frequency (RF) energy. In this manner a fluid can be conveyed through the lumen, and out through the porous structure into adjacent tissue during the ablation process. In the case where the ablative element is a single needle electrode, the needle electrode can be close ended, since perfusion of the fluid will occur through the porous structure. In general, a close ended needle electrode can penetrate through tissue more accurately. Because the pores within the porous structure are pervasive, the fluid will freely flow out into the tissue notwithstanding that some of the pores may become clogged. The porous structure may be macroporous or microporous, but in one preferred embodiment, the effective diameter of the pores will fall within the range of 1-50 microns.

The ablation probe may optionally include a sleeve disposed around the shaft, e.g., to increase the effective shear strength of the probe and/or provide electrical insulation between tissue and the probe shaft. The ablation probe may also optionally include a connector assembly mounted to the proximal end of the shaft. In this case, the connector assembly may have an perfusion inlet port in fluid communication with the lumen for conveyance of the fluid.

In accordance with a first aspect of the present invention, the porous structure has a porosity in the range of 20-80 percent, preferably within the range of 30-70 percent. In this manner, structural integrity of the shaft and/or ablative element(s) can be maintained, while providing a free flow of fluid through the many channels within the porous structure. In accordance with a second aspect of the present invention, the porous structure is microporous in order to increase the number of pores that will perfuse the fluid. In accordance with a third aspect of the present invention, the porous structure may have interconnecting pores that are arranged in a random manner, in order to provide a more efficient flow of fluid through the porous structure.

In accordance with a fourth aspect of the present invention, a tissue ablation system is provided. The system comprises an ablation probe, which may be, e.g., a surgical probe. The ablation probe comprises an ablative element (e.g., such as those previously described) and a perfusion lumen. At least a portion of the ablation probe is composed of a porous structure that is in fluid communication with the perfusion lumen. The porous structure can have the same structure and function as the previously described porous structures. The system further comprises en ablation source operably coupled to the ablative element. If the ablative element is in electrode, the ablation source can be a RF generator. The system further comprises a fluid source operably coupled to the perfusion lumen. The system may optionally comprise a pump assembly for pumping the fluid from the source through the perfusion lumen of the ablation probe.

In accordance with a fifth aspect of the present invention, a method of assembling an ablation probe is provided. The method comprises shaping a mass of particles (e.g., an electrically conductive powder) into an elongated shaft, and sintering the shaped particles to form a porous structure within the shaft. Preferably, the mass of particles are compacted prior to sintering in order to control the porosity of the porous structure. The method further comprises forming a longitudinal lumen within the shaft, which can be performed by forming the mass of particles into a hollow shaft. The method further comprises forming an ablative element on the distal end of the shaft. If the ablative element is a single needle electrode, it can be formed with the shaft during the particle shaping and sintering process. The resulting ablation probe can have the same features as the previously described ablation probe.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
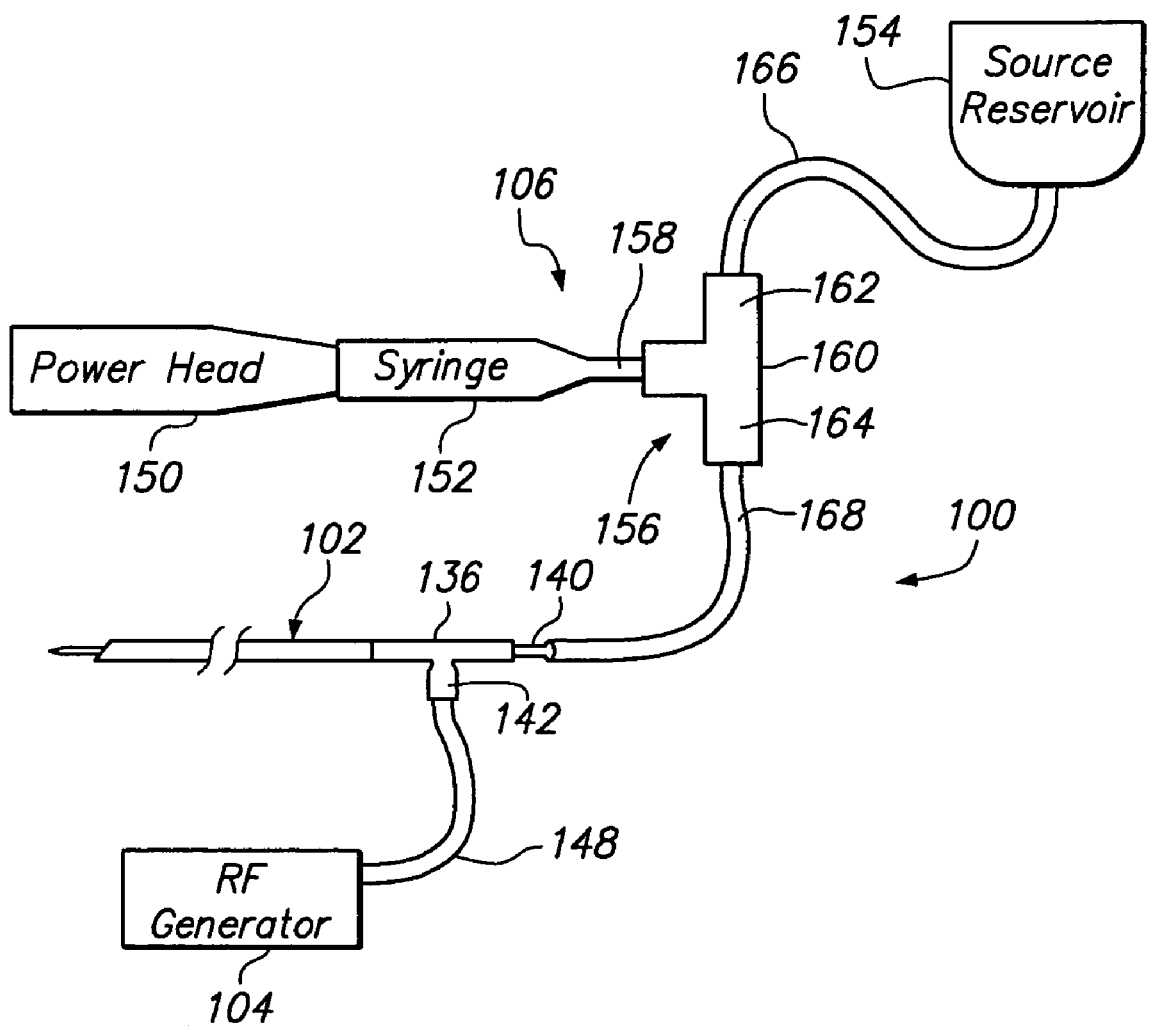
FIG. 1 is a plan view of a tissue ablation system constructed in accordance with one preferred embodiment of the present inventions.

FIG. 1 illustrates a tissue ablation system 100 constructed in accordance with a preferred embodiment of the present inventions. The tissue ablation system 100 generally comprises a probe assembly 102 configured for introduction into the body of a patient for ablative treatment of target tissue; a radio frequency (RF) generator 104 configured for supplying RF energy to the probe assembly 102 in a controlled manner; and a pump assembly 106 configured for perfusing fluid, such as saline, out through the probe assembly 102, so that a more efficient and effective ablation treatment is effected.

Figure 2:
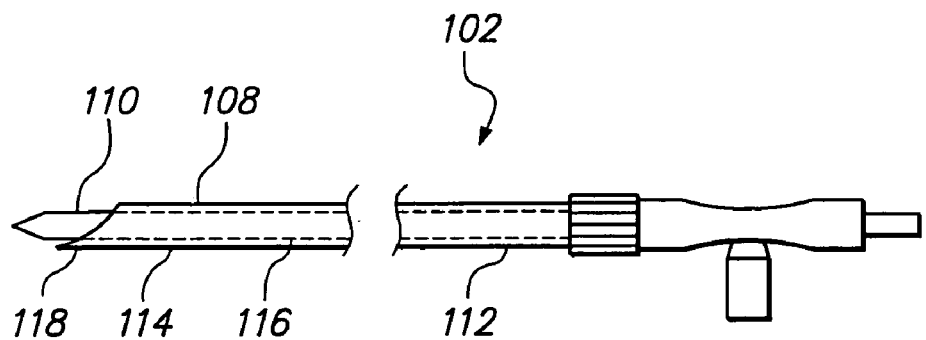
FIG. 2 is a side view of a preferred probe assembly used in the tissue ablation system of FIG. 1.

Referring specifically now to FIG. 2, the probe assembly 102 generally comprises an ablation probe 110 and a cannula 108 through which the ablation probe 110 can be introduced. As will be described in further detail below, the cannula 108 serves to deliver the active portion of the ablation probe 110 to the target tissue. The cannula 108 has a proximal end 112, a distal end 114, and a perfusion lumen 116 (shown in phantom) extending through the cannula 108 between the proximal end 112 and the distal end 114. An open tapered point 118 is formed at the distal end 114 of the cannula 108 in order to facilitate introduction of the cannula 108 through tissue. As will be described in further detail below, the cannula 108 may be rigid, semi-rigid, or flexible, depending upon the designed means for introducing the cannula 108 to the target tissue. The cannula 108 is composed of a suitable material, such as plastic, metal or the like, and has a suitable length, typically in the range from 5 cm to 30 cm, preferably from 10 cm to 20 cm. If composed of an electrically conductive material, the cannula 108 is preferably covered with an insulative material. The cannula 108 has an outside diameter consistent with its intended use, typically being from 1 mm to 5 mm, usually from 1.3 mm to 4 mm. The cannula 108 has an inner diameter in the range from 0.7 mm to 4 mm, preferably from 1 mm to 3.5 mm.

Figure 3:
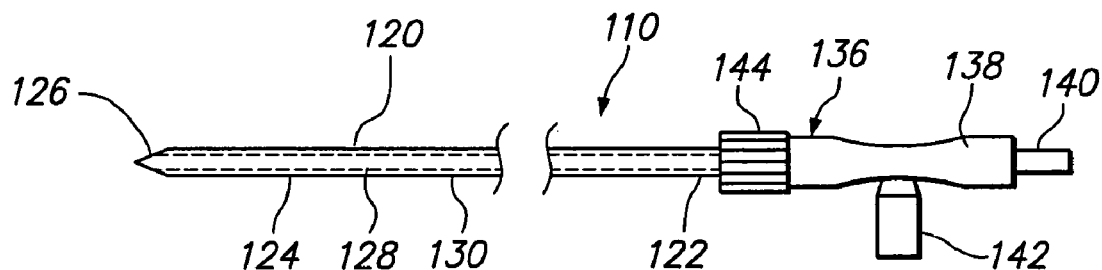
FIG. 3 is a side view of a preferred ablation probe used in the probe assembly of FIG. 2.

Referring further to FIG. 3, the ablation probe 110 generally comprises a shaft 120 having a proximal end 122 and a distal end 124, a single tissue penetrating needle electrode 126 formed at the end of the distal shaft end 124, and a lumen 128 (shown in phantom) longitudinally extending through the length of the shaft 120. The shaft 120 comprises a wall 130 that is preferably composed of an electrically conductive material, such as stainless steel, nickel-titanium alloy, nickel-chromium alloy, spring steel alloy, and the like. As will be described in further detail below, the shaft wall 130 is composed of porous structure 132, as well as the needle electrode 126, (shown in FIG. 6) that facilitates the introduction of a fluid into the tissue during the ablation process.

The needle electrode 126 is designed to penetrate into tissue as it is advanced to the target tissue site. In the illustrated embodiment, the needle electrode 126 has a closed-ended point, thereby facilitating introduction of the needle electrode 126 through the tissue along a straight line. Alternatively, the needle electrode 126 can have an open-ended tapered tip similar to the tip 118 of the cannula 108. Because the perfusion of fluid is provided through the porous structure of the shaft 120, however, the use of an open-ended tapered tip, otherwise used for perfusion, is not needed. In the illustrated embodiment, the needle electrode 126 has a circular cross-section, but may also have a non-circular cross-section as well. Like the probe shaft 120, the needle electrode 126 is composed of an electrically conductive material, such as stainless steel, nickel-titanium alloy, nickel-chromium alloy, spring steel alloy, and the like. In fact, the needle electrode 126 is preferably formed as a unibody structure with the shaft 120, as will now be described.

Figure 5:
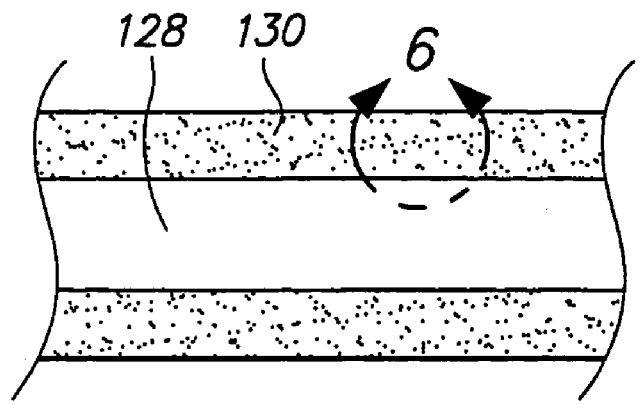
FIG. 5 is a cross-sectional view of a portion of the ablation probe of FIG. 3.
Figure 6:
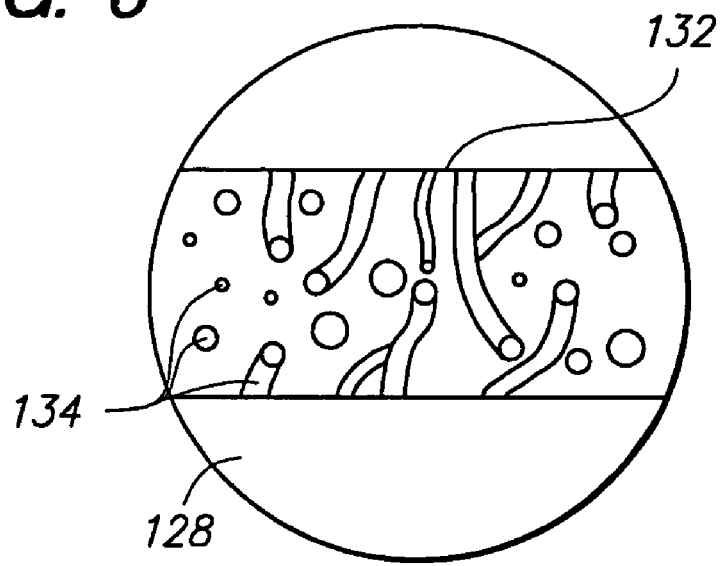
FIG. 6 is a close-up view taken along lines 6-6 in FIG. 5.

Referring to FIGS. 5 and 6, the porous structure 132 of the probe shaft 120 will now be described. The porous structure 132 comprises a plurality of pores 134 that extend through the thickness of the shaft wall 130 between the perfusion lumen 128 and exterior of the shaft 120. In the illustrated embodiment, the pores 134 are interconnected in a random interstitial arrangement in order to maximize the porosity of the shaft wall 130. The porous structure 132 may be microporous, in which case, the effective diameters of the pores 134 will be in the 0.05-20 micron range, or the porous structure 132 may be macroporous, in which case, the effective diameters of the pores 134 will be in the 20-2000 micron range. A preferred pore size will be in the 1-50 micron range. The porosity of the porous structure 132, as defined by the pore volume over the total volume of the structure, is preferably in the 20-80 percent range, and more preferably within the 30-70 percent range. Naturally, the higher the porosity, the more freely the fluid will flow through the probe wall 130. Thus, the designed porosity of the porous structure 132 will ultimately depend on the desired flow of the fluid. Of course, the porous structure 132 should not be so porous as to unduly sacrifice the structural integrity of the ablation probe 110.

Thus, it can be appreciated that the pervasiveness of the pores 134 allows the fluid to freely flow from the perfusion lumen 128, through the thickness of the shaft wall 130, and out to the adjacent tissue. Significantly, this free flow of fluid will occur even if several of the pores 134 have been clogged with material, such as tissue. For purposes of ease in manufacturability, the entire length of the probe shaft 120, including the needle electrode 126, is composed of the porous structure 132. Alternatively, only the portion of the shaft 120 that will be adjacent the ablation region (e.g., the distal shaft end 124 including the needle electrode 126) and/or the needle electrode 126 is composed of the porous structure 132.

In the preferred embodiment, the porous structure 132 is formed using a sintering process, which involves compacting a plurality of particles (preferably, a blend of finely pulverized metal powers mixed with lubricants and/or alloying elements) into the shape of the probe shaft 120, and then subjecting the blend to high temperatures.

When compacting the particles, a controlled amount of the mixed powder is automatically gravity-fed into a precision die and is compacted, usually at room temperature at pressures as low as 10 or as high as 60 or more tons/inch$^2$ (138 to 827 MPa), depending on the desired porosity of the probe shaft 120. The compacted power will have the shape of the hollow probe shaft 120 once it is ejected from the die, and will be sufficiently rigid to permit in-process handling and transport to a sintering furnace. Other specialized compacting and alternative forming methods can be used, such as powder forging, isostatic pressing, extrusion, injection molding, and spray forming.

During sintering, the unfinished probe shaft 120 is placed within a controlled-atmosphere furnace, and is heated to below the melting point of the base metal, held at the sintering temperature, and then cooled. The sintering transforms the compacted mechanical bonds between the power particles to metallurgical bonds. The interstitial spaces between the points of contact will be preserved as pores. The amount and characteristics of the porosity of the structure 132 can be controlled through powder characteristics, powder composition, and the compaction and sintering process.

Porous structures can be made by methods other than sintering. For example, pores may be introduced by mechanical perforation, by the introduction of pore producing agents during a matrix forming process, or through various phase separate techniques. Also, the porous structure may be composed of a ceramic porous material with a conductive coating deposited onto the surface, e.g., by using ion beam deposition or sputtering.

Referring back to FIG. 3, the ablation probe 110 further comprises a connector assembly 136 mounted on the proximal shaft end 122. The connector assembly 136 comprises a hollow handle piece 138 for manipulation by a physician, an perfusion inlet port 140, such as a male luer connector, and a RF port 142. The perfusion inlet port 140 is in fluid communication with the perfusion lumen 128 of the shaft 120, and the RF port 142 is in electrical communication with the shaft wall 130, and thus the needle electrode 126. The connector assembly 136 is also provided with a nut 144, which engages the threads (not shown) of the cannula 108 in order to integrate the probe assembly 102 once the needle electrode 126 is properly located at the target ablation site. The connector assembly 136 can be composed of any suitable rigid material, such as, e.g., metal, plastic, or the like.

Figure 4:
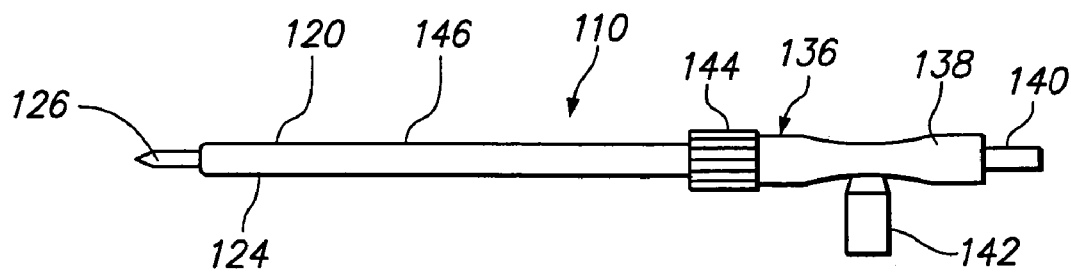
FIG. 4 is a side view of an alternative ablation probe that can be used in the probe assembly of FIG. 2.

Because the shear strength of the shaft 120 may be reduced due to its porous nature, the ablation probe 110 comprises an optional sleeve 146 that is disposed around the shaft 120 to increase the strength of the ablation probe 110 (shown in FIG. 4). Preferably, the sleeve 146 houses the entire length of the shaft 120, with the exception of the needle electrode 126, which should be exposed to allow perfusion into the target ablation site. The sleeve 146 can be formed around the shaft 120 in any one of a variety of manners, e.g., by co-extruding it over the shaft 120. If the cannula 108 is not used, or if the cannula 108 is composed of an electrically conductive material, the sleeve 146 is preferably composed of an electrically insulative material, such as plastic. In this manner, the RF energy conveyed through the shaft 120 will be concentrated at the target ablation site adjacent the needle electrode 126.

Referring back to FIG. 1, the RF generator 104 is electrically connected to the RF port 142 of the connector assembly 136 via an RF cable 148, which as previously described, is indirectly electrically coupled to the needle electrode 126 through the shaft 120. The RF generator 104 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150 V (peak-to-peak), usually being from 50 V to 100 V. The power will usually be from 20W to 200W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100W) and RF3000™ (200W).

RF current is preferably delivered from the RF generator 104 to the needle electrode 126 in a monopolar fashion, which means that current will pass from the needle electrode 126, which is configured to concentrate the energy flux in order to have an injurious effect on the surrounding tissue, and a dispersive electrode (not shown), which is located remotely from the needle electrode 126 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank.

The pump assembly 106 comprises a power head 150 and a syringe 152 that is front-loaded on the power head 150 and is of a suitable size, e.g., 200 ml. The power head 150 and the syringe 152 are conventional and can be of the type described in U.S. Pat. No. 5,279,569 and supplied by Liebel-Flarsheim Company of Cincinnati, Ohio. The pump assembly 106 further comprises a source reservoir 154 for supplying the fluid to the syringe 152. The fluid can be optionally cooled to provide the additional beneficial effect of cooling the needle electrode 126 and the surrounding tissue during the ablation process. The pump assembly 106 further comprises a tube set 156 removably secured to an outlet 158 of the syringe 152. Specifically, a dual check valve 160 is provided with first and second legs 162 and 164, of which the first leg 162 serves as a liquid inlet connected by tubing 166 to the source reservoir 154. The second leg 164 is an outlet leg and is connected by tubing 168 to the perfusion inlet port 140 on the connector assembly 136.

Thus, it can be appreciated that the pump assembly 106 can be operated to periodically fill the syringe 152 with the fluid from the source reservoir 154 via the tubing 166, and convey the fluid from the syringe 152, through the tubing 168, and into the perfusion inlet port 140 on the connector assembly 136. The fluid is then conveyed through the perfusion lumen 128 of the shaft 120, and out through the needle electrode 126. Notably, the sleeve 146 (shown in FIG. 4) prevents the fluid from perfusing out the porous structure 132 along the length of the shaft, thereby forcing all of the fluid to perfuse out of the porous structure 132 along the exposed needle electrode 126.

Other types of pump assemblies are also available for pumping fluid through the probe shaft 120. For example, a saline bag can simply be connected to the fluid inlet port 140 on the connector assembly 136 via tubing, and then raised above the patient a sufficient height to provide the head pressure necessary to convey the fluid through the shaft 120 and out of the needle electrode 126. Alternatively, pumps can be conveniently incorporated within the connector assembly 136.

The pump assembly 106, along with the RF generator 104, can include control circuitry to automate or semi-automate the cooled ablation process. Further details on the structure and operation of a controlled RF generator/pump assembly suitable for use with the tissue ablation system 100 are disclosed in U.S. Pat. No. 6,235,022, which is hereby fully and expressly incorporated herein by reference. A commercial embodiment of such an assembly is marketed as the Model 8004 RF generator and Pump System by Boston Scientific Corporation, located in San Jose, Calif.

Figure 7:
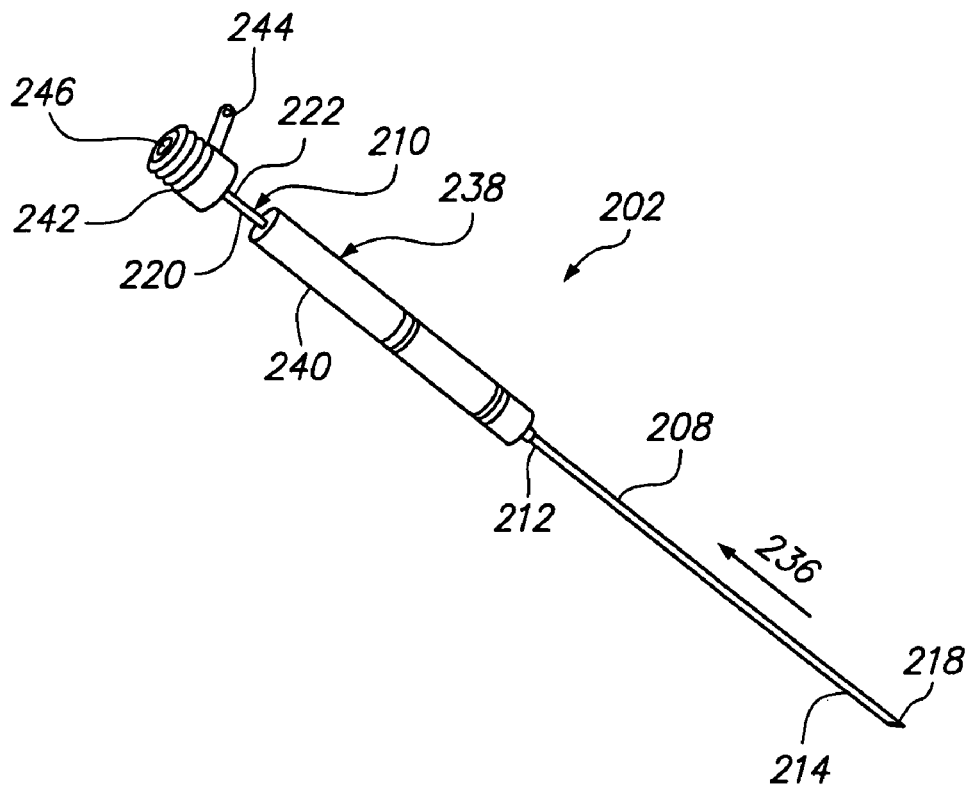
FIG. 7 is a perspective view of an alternative probe assembly that can be used in the tissue ablation system of FIG. 1, wherein the probe assembly is in its retracted state.
Figure 8:
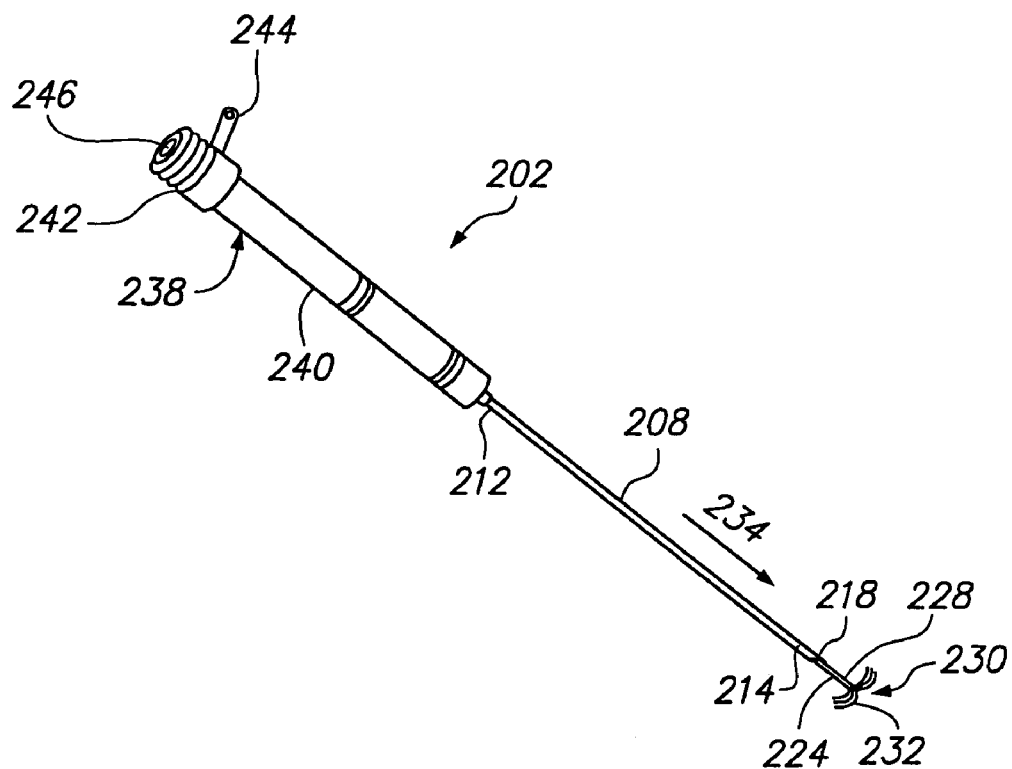
FIG. 8 is a perspective view of the probe assembly of FIG. 7, wherein the probe assembly is in its deployed state.

Referring now to FIGS. 7 and 8, an alternative embodiment of a probe assembly 202, which can be used in the tissue ablation system 100, will now be described. The probe assembly 202 generally comprises an elongated cannula 208 and an inner probe 210 slidably disposed within the cannula 208. The cannula 208 has a proximal end 212, a distal end 214, and a perfusion lumen (not shown) extending through the cannula 208 between the proximal end 212 and the distal end 214. An open tapered point 218 is formed at the distal end 214 of the cannula 208 in order to facilitate introduction of the cannula 208 through tissue. As with the cannula 108, the cannula 208 serves to deliver the active portion of the inner probe 210 to the target tissue, and may be rigid, semi-rigid, or flexible depending upon the designed means for introducing the cannula 108 to the target tissue. The cannula 208 may have the same material composition and dimensions as the cannula 108.

The inner probe 210 comprises a reciprocating shaft 220 having a proximal end 222 and a distal end 224 (shown in FIG. 8); a perfusion lumen (not shown) extending through the shaft 220 between the proximal end 222 and distal end 224; a cylindrical interface 228 mounted to the distal end 224 of the shaft 220; and an array 230 of tissue penetrating needle electrodes 232 mounted within the cylindrical interface 228. The shaft 220 is slidably disposed within the perfusion lumen of the cannula 208, such that longitudinal translation of the shaft 220 in a distal direction 234 deploys the electrode array 230 from the distal end 214 of the cannula 208 (FIG. 8), and longitudinal translation of the shaft 218 in aproxiinal direction 236 retracts the electrode array 226 230 into the distal end 214 of the cannula 108 (FIG. 7).

Like the previously described probe 110, the inner probe 210 comprises a porous structure (not shown) that allows fluid to perfuse into the target ablation site. Preferably, each of the needle electrodes 232 is composed of the porous structure. Alternatively, or optionally, the cylindrical interface 228 or the probe shaft 220, itself, can be composed of the porous structure. Thus, like the ablation probe 110, fluid may flow through the perfusion lumen of the shaft 220, and out through the porous structure of the needle electrodes 232, or alternatively the cylindrical interface 228 or shaft 220. In the case where the probe shaft 220 is composed of the porous structure, the cannula 208 will contain the fluid along the probe shaft 220, such that all of the fluid perfuses out the distal shaft end 224.

The probe assembly 202 further comprises a connector assembly 238, which includes a connector sleeve 240 mounted to the proximal end 212 of the cannula 208 and a connector member 242 slidably engaged with the sleeve 240 and mounted to the proximal end 222 of the shaft 220. The connector member 242 comprises an perfusion inlet port 244 and an RF port 246 in which the proximal ends of the needle electrodes 230 (or alternatively, intermediate conductors)

extending through the shaft 220 of the inner probe 210 are coupled. The connector assembly 238 can be composed of any suitable rigid material, such as, e.g., metal, plastic, or the like.

RF current can be delivered to the electrode array 230 in a monopolar fashion, as previously described above, or in a bipolar fashion, which means that current will pass between "positive" and "negative" electrodes 232 within the array 230. In a bipolar arrangement, the positive and negative needle electrodes 232 will be insulated from each other in any regions where they would or could be in contact with each other during the power delivery phase.

Further details regarding needle electrode array-type probe arrangements are disclosed in U.S. Pat. No. 6,379,353, entitled "Apparatus and Method for Treating Tissue with Multiple Electrodes," which is hereby expressly incorporated herein by reference.

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$ The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 9A:
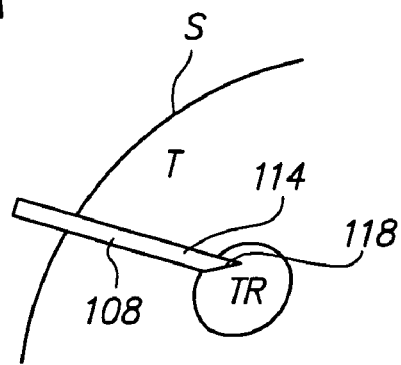
FIGS. 9A-9C illustrate cross-sectional views of one preferred method of using the tissue ablation system of FIG. 1 to treat tissue.
Figure 9B:
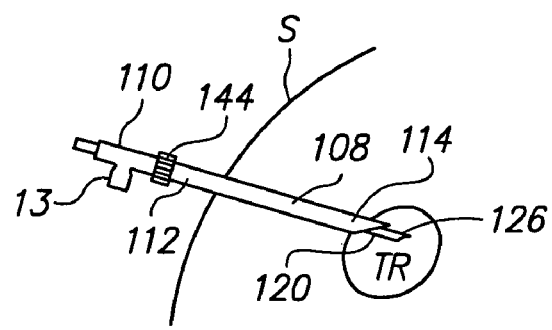
Figure 9C:
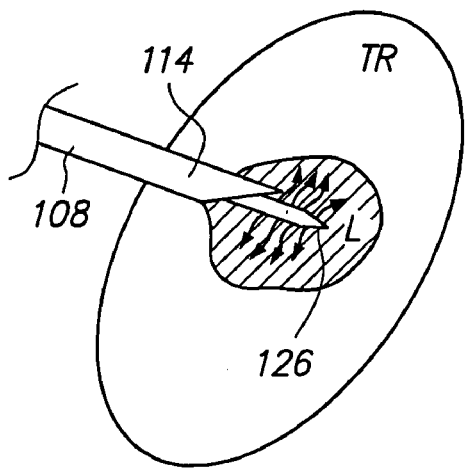

Referring now to FIGS. 9A-9C, the operation of the tissue ablation system 100 is described in treating a treatment region TR within tissue T located beneath the skin or an organ surface S of a patient. The probe assembly 102 is described in this operation, although the probe assembly 202 can be alternatively used. The cannula 108 is first introduced through the tissue T, so that the distal end 114 of the cannula 108 is located at the treatment region TR, as shown in FIG. 9A. This can be accomplished using any one of a variety of techniques. In the preferred method, the cannula 108 and probe 110 are introduced to the treatment region TR percutaneously directly through the patient's skin or through an open surgical incision. In this case, the sharpened tip 118 of the cannula 108 facilitates introduction to the treatment region TR. In such cases, it is desirable that the cannula 108 or needle be sufficiently rigid, i.e., have a sufficient column strength, so that it can be accurately advanced through tissue T. In other cases, the cannula 108 may be introduced using an internal stylet that is subsequently exchanged for the ablation probe 110. In this latter case, the cannula 108 can be relatively flexible, since the initial column strength will be provided by the stylet. More alternatively, a component or element may be provided for introducing the cannula 108 to the treatment region TR. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 108 and probe 110 can then be introduced through the sheath lumen, so that the distal end 114 of the cannula 108 advances from the sheath into the treatment region TR.

After the cannula 108 is properly placed, the probe shaft 120 is distally advanced through the cannula 108 to deploy the needle electrode 126 out from the distal end 114 of the cannula 108, as shown in FIG. 9B. Once the cannula 108 and probe 110 are properly positioned, the ablation probe 110 and cannula 108 can then be integrated with each other by threading the nut 144 around the threaded potion of the cannula proximal end 112. The RF generator 104 is then connected to the connector assembly 136 via the RF port 142, and the pump assembly 106 is connected to the connector assembly 136 via the fluid inlet port 140, and then operated to ablate the treatment region TR, while perfusing the treatment region TR with fluid, as illustrated in FIG. 9C. As a result, lesion L will be created, which will eventually expand to include the entire treatment region TR.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An ablation probe, comprising:
    an elongated shaft having a distal end;
    an ablative element disposed on the distal end of the shaft;
    a lumen longitudinally extending within the shaft; and
    a porous structure extending along a substantial entirety of the shaft in fluid communication with the lumen, the porous structure having pores with effective diameters in the range of 1-50 microns, the entirety of the porous structure being composed of a metallic substance.

2. The ablation probe of claim 1, wherein the porous structure has a porosity in the range of 30-70 percent.

3. The ablation probe of claim 1, wherein the shaft is a rigid shaft.

4. The ablation probe of claim 1, wherein the porous structure is electrically conductive.

5. The ablation probe of claim 1, wherein the porous structure is composed of a metallic substance.

6. The ablation probe of claim 1, wherein the porous structure has a porosity in the range of 20-80 percent.

7. The ablation probe of claim 1, wherein the porous structure has interconnecting pores.

8. The ablation probe of claim 1, wherein the entirety of the shaft is composed of the porous structure.

9. The ablation probe of claim 1, wherein the ablative element comprises at least one electrode.

10. The ablation probe of claim 1, further comprising a connector assembly mounted to a proximal end of the shaft, wherein the connector assembly comprises a port in fluid communication with the lumen.

11. The ablation probe of claim 1, further comprising a handle mounted to a proximal end of the shaft.

12. An ablation probe, comprising:
    an elongated shaft having a distal end;
    an ablative element disposed on the distal end of the shaft;
    a lumen longitudinally extending within the shaft; and
    a microporous structure extending along a substantial entirety of the shaft in fluid communication with the lumen, the entirety of the microporous structure being composed of a metallic substance.

13. The ablation probe of claim 12, wherein the shaft is a rigid shaft.

14. The ablation probe of claim 12, wherein the microporous structure is electrically conductive.

15. The ablation probe of claim 12, wherein the microporous structure has interconnecting pores.

16. The ablation probe of claim 12, wherein the ablative element is composed of the microporous structure.

17. The ablation probe of claim 12, wherein the ablative element comprises at least one electrode.

18. The ablation probe of claim 12, wherein the microporous structure is composed of a metallic substance.

19. The ablation probe of claim 12, further comprising a connector assembly mounted to a proximal end of the shaft, wherein the connector assembly comprises a port in fluid communication with the lumen.

20. The ablation probe of claim 1, wherein the entirety of the shaft is composed of the microporous structure.

21. The ablation probe of claim 12, further comprising a handle mounted to a proximal end of the shaft.

22. An ablation probe, comprising:
an elongated shaft having a distal end;
an ablative element disposed on the distal end of the shaft;
a lumen longitudinally extending within the shaft; and
a porous structure extending along a substantial entirety of the shaft in fluid communication with the lumen, the porous structure having interconnecting pores, the entirety of the porous structure being composed of a metallic substance.

23. The ablation probe of claim 22, wherein the pores are interconnected in a random arrangement.

24. The ablation probe of claim 22, wherein the shaft is a rigid shaft.

25. The ablation probe of claim 22, wherein the porous structure is electrically conductive.

26. The ablation probe of claim 22, wherein the ablative element is composed of the porous structure.

27. The ablation probe of claim 22, wherein the ablative element comprises at least one electrode.

28. The ablation probe of claim 22, further comprising a connector assembly mounted to a proximal end of the shaft, wherein the connector assembly comprises a port in fluid communication with the lumen.

29. The ablation probe of claim 22, wherein the entirety of the shaft is composed of the porous structure.

30. The ablation probe of claim 22, further comprising a handle mounted to a proximal end of the shaft.

31. A tissue ablation system, comprising:
an ablation probe having an ablative element and a perfusion lumen, substantially the entire length of the ablation probe being composed of a porous structure in fluid communication with the perfusion lumen, the porous structure having pores with effective diameters in the range of 1-50 microns, the entirety of the porous structure being composed of a metallic substance;
an ablation source operably coupled to the ablative element; and
a fluid source operably coupled to the perfusion lumen.

32. The tissue ablation system of claim 31, wherein the porous structure has a porosity in the range of 30-70 percent.

33. The tissue ablation system of claim 31, wherein the porous structure is electrically conductive.

34. The tissue ablation system of claim 31, wherein the porous structure has interconnecting pores.

35. The tissue ablation system of claim 31, wherein the ablation probe is a rigid probe.

36. The tissue ablation system of claim 31, wherein the ablative element comprises at least one electrode.

37. The tissue ablation system of claim 31, wherein the ablation source is a radio frequency (RF) ablation source.

38. The tissue ablation system of claim 31, further comprising a pump assembly for pumping fluid from the fluid source and through the perfusion lumen of the ablation probe.

39. The tissue ablation system of claim 31, wherein the ablation probe comprises a shaft, the entirety of which is composed of the porous structure.

40. The tissue ablation system of claim 31, further comprising a handle mounted to a proximal end of the shaft.

41. A tissue ablation system, comprising:
an ablation probe having an ablative element and a perfusion lumen, substantially the entire length of the ablation probe being composed of a microporous structure in fluid communication with the perfusion lumen, the entirety of the micrororous structure being composed of a metallic substance;
an ablation source operably coupled to the ablative element; and
a fluid source operably coupled to the perfusion lumen.

42. The tissue ablation system of claim 41, wherein the porous structure has interconnecting pores.

43. The tissue ablation system of claim 41, wherein the ablation probe is a rigid probe.

44. The tissue ablation system of claim 41, wherein the ablative element comprises at least one electrode.

45. The tissue ablation system of claim 41, wherein the ablation source is a radio frequency (RF) ablation source.

46. The tissue ablation system of claim 41, further comprising a pump assembly for pumping fluid from the fluid source and through the perfusion lumen of the ablation probe.

47. The tissue ablation system of claim 41, wherein the ablation probe comprises a shaft, the entirety of which is composed of the microporous structure.

48. The tissue ablation system of claim 41, further comprising a handle mounted to a proximal end of the shaft.

49. A tissue ablation system, comprising:
an ablation probe having an ablative element and a perfusion lumen, substantially the entire length of the ablation probe being composed of a porous structure in fluid communication with the perfusion lumen, the porous structure having interconnecting pores, the entirety of the porous structure being composed of a metallic substance;
an ablation source operably coupled to the ablative element; and
a fluid source operably coupled to the perfusion lumen.

50. The tissue ablation system of claim 49, wherein the pores are interconnecting in a random arrangement.

51. The tissue ablation system of claim 49, wherein the ablation probe is a rigid probe.

52. The tissue ablation system of claim 49, wherein the ablative element comprises at least one electrode.

53. The tissue ablation system of claim 49, wherein the ablation source is a radio frequency (RF) ablation source.

54. The tissue ablation system of claim 49, further comprising a pump assembly for pumping fluid from the fluid source and through the perfusion lumen of the ablation probe.

55. The tissue ablation system of claim 49, wherein the ablation probe comprises a shaft, the entirety of which is composed of the porous structure.

56. The tissue ablation system of claim 49, further comprising a handle mounted to a proximal end of the shaft.

* * * * *